United States Patent [19]
Edwards et al.

[11] Patent Number: 6,132,579
[45] Date of Patent: Oct. 17, 2000

[54] LIQUID SEPARATION

[75] Inventors: Stephen J. Edwards; Stephanie J. McIntyre, both of Pinner, United Kingdom

[73] Assignee: Eastman Kodak Company, Rochester, N.Y.

[21] Appl. No.: 09/236,872

[22] Filed: Jan. 26, 1999

[30] Foreign Application Priority Data

Feb. 9, 1998 [GB] United Kingdom ................. 9802600

[51] Int. Cl.[7] .................... G01N 27/26; G01N 27/447
[52] U.S. Cl. .................... 204/451; 204/450; 204/452; 204/453; 204/600; 204/601; 204/603; 204/604
[58] Field of Search .................... 204/450, 451, 204/452, 453, 454, 455, 600, 601, 602, 603, 604, 605

[56] References Cited

U.S. PATENT DOCUMENTS

| | | | |
|---|---|---|---|
| 3,956,099 | 5/1976 | Israel et al. | 204/615 |
| 4,375,401 | 3/1983 | Catsimpoolas | 204/607 |
| 4,715,943 | 12/1987 | Place et al. | 204/612 |
| 5,413,686 | 5/1995 | Klein et al. | 204/603 |
| 5,585,069 | 12/1996 | Zanzucchi et al. | 204/600 X |
| 5,872,010 | 2/1999 | Karger et al. | 204/451 X |

FOREIGN PATENT DOCUMENTS

94/03631  2/1994  WIPO.

*Primary Examiner*—Jill Warden
*Assistant Examiner*—John S. Starsiak, Jr.
*Attorney, Agent, or Firm*—Frank Pincelli

[57] ABSTRACT

A liquid is separated into its constituent species by electrophoresis along a capillary channel. A plurality of the channels is provided in the thickness of an injection molded plastics disc. The disc is rotatably mounted such that samples are dispensed into successive channels. When all twelve channels have been used, the disc is replaced with a fresh one.

14 Claims, 3 Drawing Sheets

LIQUID SEPARATION

FIELD OF THE INVENTION

This invention relates to the separation of liquid into its constituents by the application thereto of an electric field.

BACKGROUND OF THE INVENTION

It may be desired to analyze a liquid not, or not only, for its bulk properties, but for the properties of its constituents, for example, properties of its ionic species. Therefore, the constituents have to be separated. It is known to do this by electrophoresis, including isotachophoresis, in which a sample of liquid is introduced into one end of a capillary tube and is subjected to an electric field. The sample, or constituents thereof, moves along the tube under the influence of the field, separating, for example into its various species, depending on their mobilities. Analysis can then be carried out on the individual species.

It is one object of the present invention to provide apparatus for and a method of separating liquid into its constituents in a particularly convenient manner.

SUMMARY OF THE INVENTION

In accordance with one aspect of the present invention, there is provided apparatus for separating liquid into its constituents by the application thereto of an electric field, comprising a disc that is rotatably mounted about an axis substantially perpendicular to the plane thereof, the disc having at least two discrete capillary channels for liquid samples, wherein the ratio of the length to the maximum transverse dimension of each channel is at least about 100:1, and wherein each channel (a) has an inlet at one end for receiving a liquid sample, (b) has at least one electrode at each end for applying an electric field to the sample thereby to cause the sample, or constituents thereof, to be driven towards the other end and to be longitudinally separated into its constituents, and (c) has means at said other end for detecting the separated constituents of the liquid sample.

It is to be understood that reference to a component of the apparatus being "at" an end of a channel includes the component being adjacent thereto.

Preferably, the channels are formed in the thickness of the disc. The disc may be formed from two plates secured together, and the channels may then extend across the interface, or alternatively may be formed in one of the plates, the other plate forming a lid. The disc, of electrically insulating material, may be formed from a plastics material, or from glass. The disc may be injection molded, and the channels may be formed therein during this process.

At least one, and preferably each, of the channels may extend between the periphery and a central region of the disc. At least one, and preferably each, of the channels may extend substantially linearly, or in a serpentine path, in the plane of the disc. The liquid inlets may be at the inner or at the outer end of the channels.

The channel dimension ratio is preferably between about 200 and about 500.

Each channel may be of rectilinear, circular, V- or U-configuration.

The detection means may detect the separated components electrochemically, electrically or optically. For example, the detection means may comprise a set of electrodes for detecting the different electrical conductivity of the separated constituents. Alternatively, the refractive index or the color of the constituents may be used to differentiate them. In another embodiment, the differentiation may be carried out electrochemically, for example using a silver electrode. Although in general the same means of detection would be used for each of the channels of a single disc, it is envisaged that different means may be employed from one channel to another.

The apparatus may comprise means for effecting the rotation of the disc so as to dispose the inlets of successive channels adjacent a liquid dispenser.

The disc may be mounted on a support arrangement of the apparatus so that it is interchangeable with a fresh disc.

The apparatus may comprise means at said other end of each channel for analyzing the separated constituents of the sample, for example electrochemically, electrically or chemically using voltammetry, potentiometry, titration, conductivity, colormetric or optical analysis.

In accordance with another aspect of the present invention, there is provided a method of separating a plurality of liquid samples into their constituents, wherein a sample is dispensed into an inlet at one end of a channel of a disc, the disc is rotated and another sample is dispensed into an adjacent channel, applying a voltage between electrodes at each end of each channel so as to drive the samples, or constituents thereof, along their respective channels to the other ends thereof, and detecting the separated constituents at said other ends of each of the channels, and wherein the ratio of the length to the maximum transverse dimension of each channel is at least about 100:1.

The disc may have at least three of said channels and may be rotated so that successive liquid samples are dispensed into adjacent channels.

The separation of the constituents of each sample may be carried out electrically or optically.

The separated constituents may be analyzed.

The liquid separating apparatus of the present invention is particularly suited for operation with a plurality of samples in a quick and convenient manner. When the disc is interchangeable, the apparatus is particularly suited for inexpensive, single-use operation.

BRIEF DESCRIPTION OF THE DRAWINGS

Apparatus for and a method of separating liquid into its constituents, will now be described, by way of example, with reference to the accompanying drawings, in which.

DETAILED DESCRIPTION OF THE INVENTION

Figure 1:
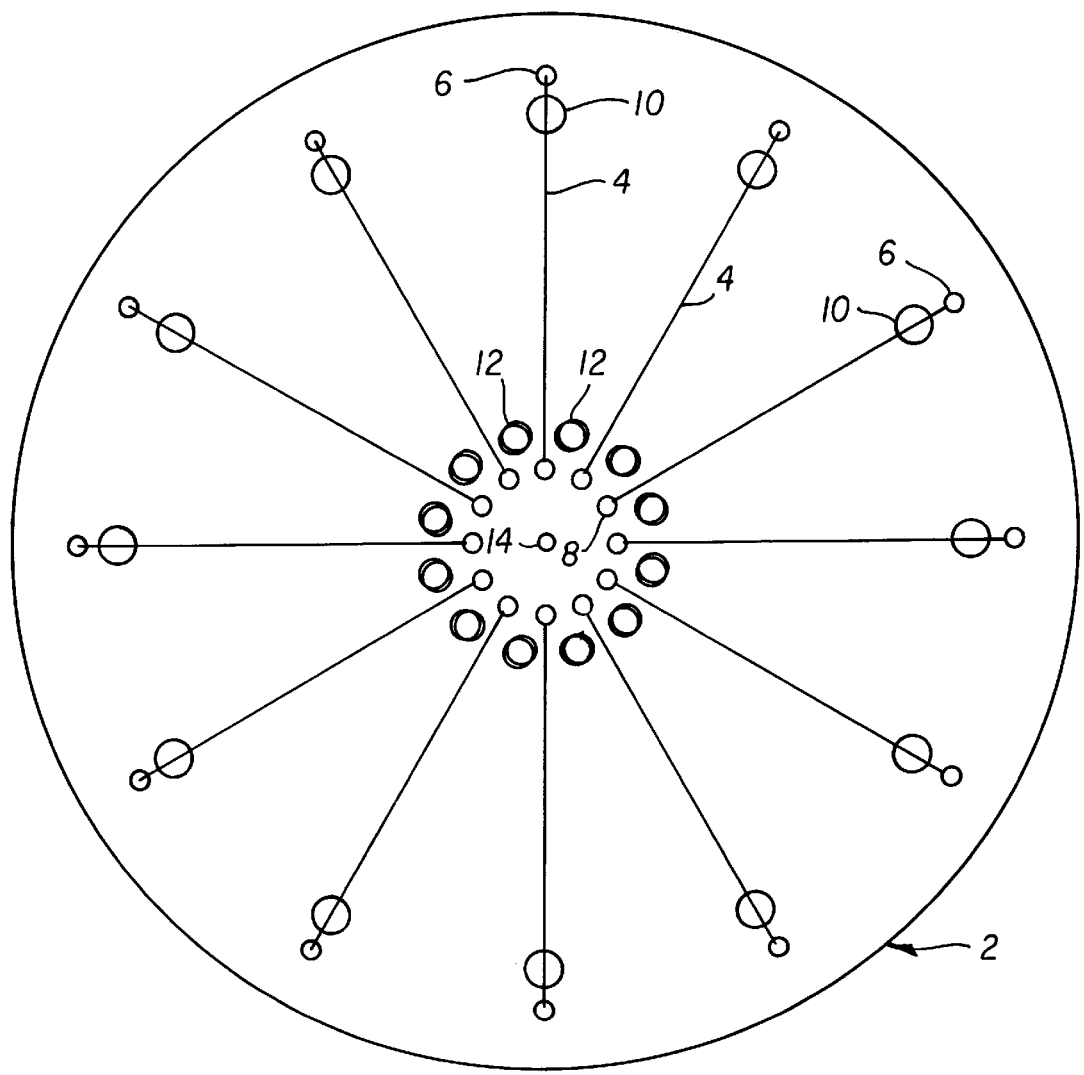
FIG. 1 is a schematic plan view of one embodiment of the disc of the apparatus.
Figure 3:
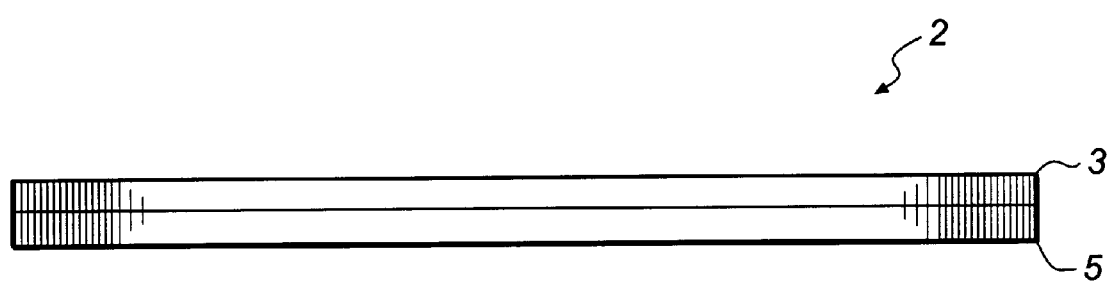
FIG. 3 is a side elevational view of the disc of FIG. 1.

Referring to FIGS. 1 and 3, a disc 2, comprising of plates 3 and 5, of diameter 15 cms and thickness 0.5 cms is injection molded from a plastics material. The disc 2 contains twelve equispaced capillary channels 4 extending radially through the body thereof. Each channel 4 is 10 cms long, 300$\mu$ wide and 60$\mu$ deep. A first set of electrodes 6 and a second set of electrodes 8 are molded into the disc 2 at the outer and inner ends respectively of the channels 4. A respective sample well 10 in the upper surface of the disc 2 communicates with each channel 4 adjacent its outer end electrode 6.

In operation, a sample of the liquid whose chemical species are to be separated for analysis is introduced from a dispenser (not shown) into the well 10 at the outer end of one of the channels 4, and a high voltage, of 1500V, is applied between the electrodes 6 and 8 of that channel 4. The electric field causes the sample, or constituents thereof, to move towards the inner end of the channel 4, and in so doing the species separate along the channel 4 in accordance with their different mobilities. The strength of the electric field for a given length of channel 4 is chosen with respect to the liquid being sampled so that complete separation takes place before the sample reaches the inner end of the channel 4.

The separated species of the liquid sample are detected at the inner end of the channel 4 by a pair of electrodes 12, which respond to the different electrical conductivities thereof. The species may then be treated separately, for example by electrical, electrochemical or optical analysis.

The disc 2 is then rotated about its vertical axial shaft 14 so as to dispose the well 10 of the next channel 4 beneath the dispenser.

The next sample is then dealt with as above. The second sample may be of the same liquid as, or different from, the first. The detector at the inner end of the second channel 4 may be the same as, or different from, that of the first. The analysis carried out on the second sample may be the same as, or different from, that carried out on the first.

The disc 2 is successively rotated until a sample has been dealt with in each of the twelve channels 4.

Owing to the comparatively high electric field that extends along the channels 4, it is important that they be sufficiently separated from each other to avoid any interference therebetween.

The arrangement of channels in the disc need not be radial as shown in FIG. 1. A modification is shown in FIG. 2, in which the detector electrodes have been omitted for clarity.

Figure 2:
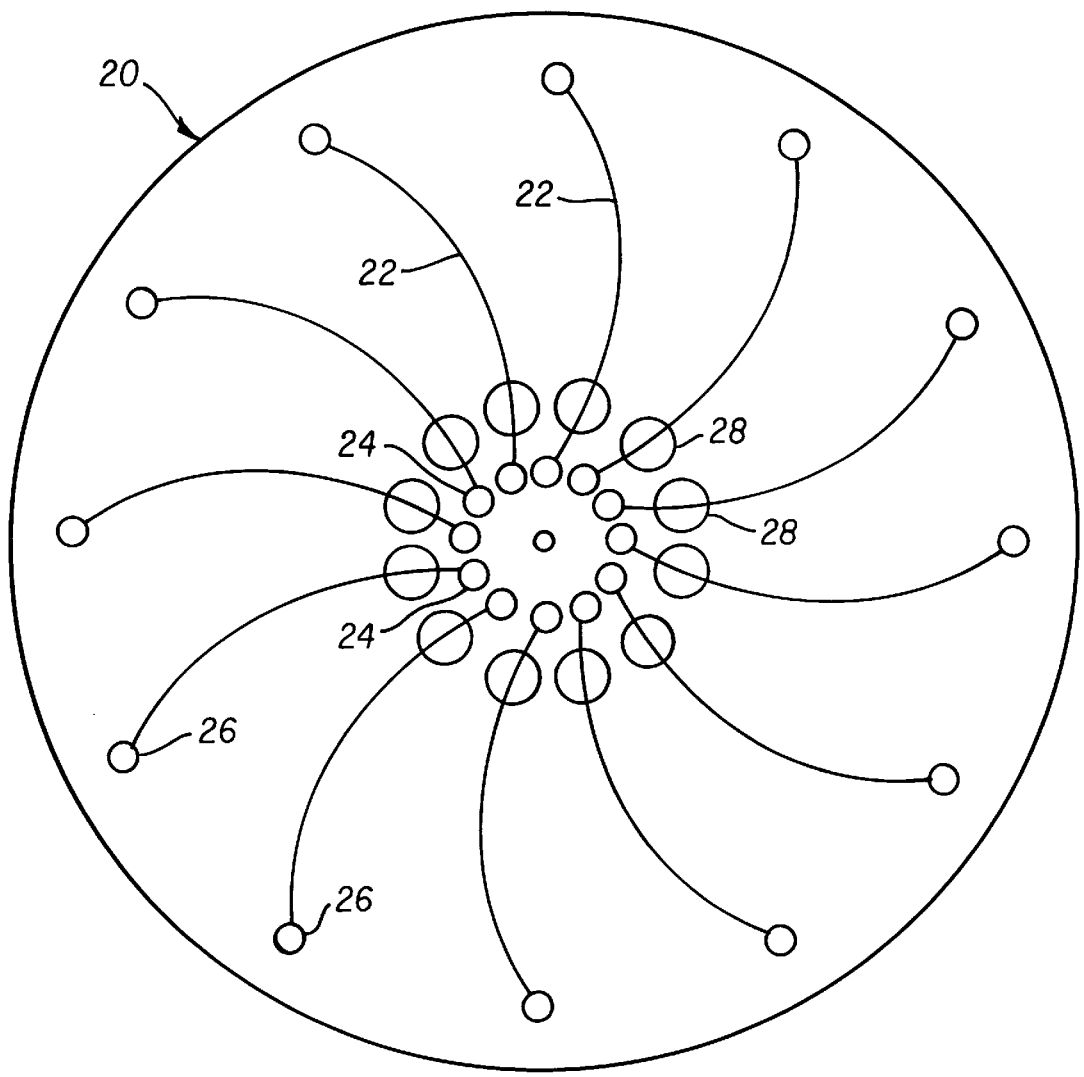
FIG. 2 is a simplified schematic plan view of a modified disc.

Referring to FIG. 2, a disc 20 has twelve channels 22 that extend in curves between respective inner and outer electrodes 24 and 26, with respective sample inlets 28 located at the inner ends thereof. Such a path allows the channels 22 to have an increased length with respect to the linear paths of the channels 4 whilst maintaining the same disc diameter.

It will be appreciated that the channels may follow paths different from those exemplified in the Figures.

The invention has been described in detail with particular reference to preferred embodiments thereof, but it will be understood that variations and modifications can be effected within the scope of the invention.

PARTS LIST 2 disc
4 channels
6 electrodes
8 electrodes
10 well
12 electrodes
14 vertical axial shaft
20 disc
22 channels
24 electrodes
26 electrodes
28 inlets

What is claimed is:

1. Apparatus for separating liquid into its constituents by the application thereto of an electric field, comprising a disc that is rotatably mounted about an axis substantially perpendicular to the plane thereof, the disc having at least two discrete channels for liquid samples, wherein the ratio of the length to the maximum transverse dimension of each channel is at least about 100:1, and wherein each channel (a) has an inlet at one end for receiving a liquid sample, (b) has at least one electrode at each end for applying an electric field to the sample thereby to cause the sample, or constituents thereof, to be driven towards the other end and to be longitudinally separated into its constituents, and (c) has means at said other end for detecting the separated constituents of the liquid sample.

2. Apparatus according to claim 1, wherein the channels are formed in the thickness of the disc.

3. Apparatus according to claim 2, wherein the disc is formed from two plates secured together.

4. Apparatus according to claim 1, wherein the disc is formed from two plates secured together.

5. Apparatus according to claim 1, wherein at least one, and preferably each, of the channels extends between the periphery and a central region of the disc.

6. Apparatus according to claim 1, wherein at least one, and preferably each, of the channels extends substantially linearly in the plane of the disc.

7. Apparatus according to claim 1, wherein at least one, and preferably each, of the channels extends in a serpentine path in the plane of the disc.

8. Apparatus according to claim 1, wherein the channel dimension ratio is between about 200 and about 500.

9. Apparatus according to claim 1, wherein each channel is of rectilinear configuration.

10. Apparatus according to claim 1, wherein the detection means detects the separated components electrochemically, electrically or optically.

11. A method of separating a plurality of liquid samples into their constituents using a disc having a plurality of channels, each of said channels having an inner end at one end and an outer end at the other end, the ratio of the length to the maximum transverse dimension of each of said channels being at least about 100:1, comprising the steps of:
    a. dispensing a sample into said outer end of one of said channels of said disc;
    b. applying a voltage between electrodes at each of said ends of each channel so as to drive the sample, or constituents thereof, along the channel to the associated exit;
    c. detecting the separated constituents at said exit end of the channel;
    d. rotating said disc to a subsequent position and dispensing another sample into said outer end of an adjacent channel; and
    e. repeating steps b, c, and d until all of said channels are used.

12. A method according to claim 11, wherein the disc has at least three of said channels and is rotated so that successive liquid samples are dispensed into adjacent channels.

13. A method according to claim 12, wherein the separated constituents are analyzed.

14. A method according to claim 11, wherein the separated constituents are analyzed.

* * * * *